(12) United States Patent
Duncan et al.

(10) Patent No.: US 7,678,393 B1
(45) Date of Patent: Mar. 16, 2010

(54) MIXTURE COMPOSITION AND METHOD USEFUL FOR TOPICAL AND INTERNAL APPLICATION

(75) Inventors: Bradford Ray Duncan, Kooskia, ID (US); David Daniel Bernhard, Kooskia, ID (US)

(73) Assignee: DB Laboratories LLC, Stites, ID (US)

( * ) Notice: Subject to any disclaimer, the term of this patent is extended or adjusted under 35 U.S.C. 154(b) by 0 days.

(21) Appl. No.: 11/738,797

(22) Filed: Apr. 23, 2007

Related U.S. Application Data

(60) Provisional application No. 60/745,405, filed on Apr. 23, 2006.

(51) Int. Cl.
| | |
|---|---|
| A61K 36/87 | (2006.01) |
| A61K 36/22 | (2006.01) |
| A61K 36/00 | (2006.01) |
| A61K 36/752 | (2006.01) |
| A61K 33/38 | (2006.01) |

(52) U.S. Cl. .................. 424/725; 424/766; 424/736; 424/618

(58) Field of Classification Search .................. None
See application file for complete search history.

(56) References Cited

U.S. PATENT DOCUMENTS

| 4,265,913 | A | * | 5/1981 | Eichelburg | |
| 5,912,363 | A | | 6/1999 | Nafisi-Movaghar et al. | |
| 2003/0008048 | A1 | * | 1/2003 | Winston et al. | 426/548 |
| 2004/0082539 | A1 | | 4/2004 | Kelly | |
| 2005/0186147 | A1 | * | 8/2005 | Tamarkin et al. | 424/47 |
| 2006/0182787 | A1 | * | 8/2006 | Jaenichen et al. | 424/445 |

FOREIGN PATENT DOCUMENTS

| DE | 102004002168 A1 | * | 8/2005 |
| GB | 2385768 A | * | 9/2003 |
| JP | 2004284988 A | * | 10/2004 |

OTHER PUBLICATIONS

Hu et al, Study on antioxidative an free oxygen radical scavenging activity of Juglans, Shipin Gongye Keji (2002), 23 (3), 15-16.*
Pinnell et al, The benefits of topical vitamin C (L-ascorbic acid) for skin care and UV protection, Journal of Applied Cosmetology, 1999: 17 (4): 126-134.*
Daels-Rakotoarison et al, Effects of *Rosa canina* fruit extrat on neutrophil respiratory brust, Phytotherapy research 16, 157-161, 2002.*
Rane et al, Comparative effect of oral administration and topical application of alcoholic extract of *Terminalia arjuna* bark on incision and excision wounds in rats, Fitoterapia 74 (2003) 553-558.*
Khanna et al, Dermal wound healing properties of redox-active grape seed proanthocyanidins, Free radical biology & Medicine, 33 (8): 1089-1096, 2002.*
Lin et al, Antoxidant, antimutagenic and immunomodulatory potentials of Gynura bicolar and Amaranthus gangetcaue, Taiwanese journal of agricultural chemistry and food science (2004), 42 (4): 231-241.*
Miyake et al, Isolation of eriocitrin (Eriodictyol 7-rutinoside) from lemon fruit (Citrus limon brum. F.) and its antioxidative activity, Food Sci Technol Int Tokyo, 3 (1), 84-89, 1997.*
Matito et al, Antiproliferative effect of antioxidant polyphenols from grape in murine Hepa-1c1c7, Eur J Nutr 42: 43-40 (2003).*
Skin disorder from Merck Manual, pp. 1-2, Accessed Feb. 3, 2009.*
Vitiligo from Merck Manual, pp. 1-2, Accessed Feb. 3, 2009.*
Yu et al, Effects of long-term oral administration of polymeric microcapsules containing tyrosinase on maintaining decreased systemic tyrosine levels in rats, Journal of pharmaceutical sciences, (Apr. 2004) vol. 93, No. 4, pp. 831-837.*
Cleaver, Defective repair replication of DNA in xeroderma pigmentosum, Nature [London], (1968) vol. 218, No. 5142, pp. 652-656.*
Gura, Systems for indentifying new drugs are often faulty, Science, v278, 1997, pp. 1041-1042.*
Freshney, Culture of Animal Cells, A Manual of Basic Technique, Alan R. Liss, Inc., 1983, New York, p. 4.*
Dermer, Another anniversary for the war on cancer, Bio/Technology, 1994, 12: 320.*
Disorders from Merck Manual, pp. 1-2, Accessed Mar. 24, 2009.*
Mohamad, Pharmacotherapy of multiple myeloma, Expert opinion on pharmacotherapy, (Apr. 2006) vol. 7, No. 6, pp. 767-781.*
Agarwal et al, Epidemiology of dog bites: a community-based study in India, Tropical doctor, (Apr. 2004) vol. 34, No. 2, pp. 76-78.*

(Continued)

*Primary Examiner*—Michele Flood
*Assistant Examiner*—Qiuwen Mi

(57) ABSTRACT

A mixture composition useful in wound healing comprising solvent extraction of anthrocyanin/proanthrocyanidin sources, ascorbic acid source, tannin or gallic acid source or polymeric gallic acid source, microbe source, protein source, fat source, acidification agent or buffer and sulfur absorbing compound.

1 Claim, No Drawings

OTHER PUBLICATIONS

Edith et al, Pharmacologic approaches to the treatment of amyotrophic lateral sclerosis, BioDrugs : clinical immunotherapeutics, biopharmaceuticals and gene therapy, (2005) vol. 19, No. 1, pp. 31-37.*

Tara et al, Nature, nurture and neurology: gene-environment interactions in neurodegenerative disease. FEBS Anniversary Prize Lecture delivered on Jun. 27, 2004 at the 29th FEBS Congress in Warsaw, The FEBS journal, (May 2005) vol. 272, No. 10, pp. 2347-2361.*

Larson, R. A., Naturally Occurring Antioxidants, 1997, Lewis Publisher, Boca Raton, New York, USA.

Takedo, K. and Okumura, K. (2004) Evidenced-based Complimentary and Alternative Medicine, 1(1): 17-27.

Bruneton, J., Pharmacognosy, 1999, 383, Lavoisier Publishing, Paris, France.

Elliot Jr., E.,Kandaswami, C. and Theoharides, T.C. (2000) The American Society for Pharmacology and Experimental Therapeutics 52(4): 673-751.

Lee, B., Jung, S. Lee, J. et al. (2005) Molecules and Cell 20(1): 69-73.

Janssen, S. and Beyaert, R. (Oct. 2003) Clinical Microbiology Reviews 16(4): 637-646.

Henderson, B., Poole, S. and Wilson, M. (Jun. 1996) Microbiology Reviews 60(2) 316-341.

Hessle, C., Andersson, B. and Wold, A. E. (Jun. 2000) Infection and Immunity 68(6): 3581-3586.

Plitnick, L. M., Jordan, R. A., Banas, J. A., Jelley-Gibbs, D. M., Walsh, M. C., Preissler, M. T. and Gosselin, E. J. (Sep. 2001) Clinical and Diagnostic Laboratory Immunology 8(5): 972-979.

Tsai, G. -J. and Cousin, M. A. (Aug. 1993) Applied and Environmental Microbiology 59(8): 2563-2571.

Martin, N., Berger C., Le Du, C. and Spinnler, H. E. (2001) Journal of Dairy Science 84(10): 2125-2135.

Rimek, D., Singh, J. and Kappe, R. (Jul. 2003) Journal of Clinical Microbiology 41(7): 3395-3398.

Xu, Q. (Jul. 2002) Arterioscler. Thromb. Vasc. Biol. 22:1547-1559.

Rusak, G., Gutzeit, H. O. and Ludwig-Muller, J. (2002) Food Technol. Biotechnol. 40(4): 267-273.

Fatehi, M., Jafarzadeh, M., Fatehi-Hassanabad, Z. and Gholamnezhad, Z. (2006) DARU 14(1): 6-10.

Faure, V., Courtois, Y. and Goureau, O. (1998) American Physiology Society C208-C215.

Ryan, K. A., Smith Jr., M. F., Sanders, M. K. and Ernst, P. B. (Apr. 2004) Infection and Immunity 72(4): 2123-2130.

Lee, C., Chien, C. and Yang, C. (2004) Am. J. Physiol. Lung Cell Mol. Physiol. 286: L921-L930.

Liang, Y., Huang, Y., Tsai, S., Lin-Shiau, S., Chen, C. and Lin, J. (1999) Carcinogenesis 20(10): 1945-1952.

Zheng, J. and Ramirez, V. (2000) British Journal of Pharmacology 130: 1115-1123.

Garg, A., Buchholz, T. and Aggarwal, B. (2005) Antioxidants and Redox Signaling 7(11&12): 1630-1647.

Suhr, Y. and Kunda, J. (2005) Archives of Pharmacal Research 28(1): 1-15.

Chen, W. and Lin, J. (Apr. 2004) The Journal of Biological Chemistry 279(14): 13496-13505.

Giannasca, P. J., Boden, J. A. and Monath, T. P. (Oct. 1997) Infection and Immunity 65(10): 4288-4298.

Iwasaki, A. and Kelsall, B. (Jul. 1999) The Journal of Experimental Medicine 190(2): 229-239.

Levels, J. H. M., Abraham, P. R., Van Barreveld, E. P., Meijers, J. C. M. and Van Deventer, S. J. H. (Jun. 2003) Infection and Immunity 71(6): 3280-3284.

Wurfel, M. M., Hailman, E. and Wright, S. D. (May 1995) The Journal of Experimental Medicine 181: 1743-1745.

Libby, P. (May 2002) Scientific American 286(5): 47-55.

Schewe, T., Kuhn, H. and Sies, H. (2002) Journal of Nutrition 132: 1825-1829.

Vasserot, Y., Caillet, S. and Maujean, A. (1997) Am. J. Enol. Vitic. 48: 433-437.

Moghimi, S. M., Hunter, A. C. and Murry, J. C. (2001) Pharmacological Reviews 53(2): 283-318.

Deprez, S., Brezillon, C., Rabot, S., Phillippe, C. Mila, I., Lapierre, C. and Scalbert, A. (2000) Journal of Nutrition 130: 2733-2738.

* cited by examiner

MIXTURE COMPOSITION AND METHOD USEFUL FOR TOPICAL AND INTERNAL APPLICATION

FIELD OF THE INVENTION

The present invention relates to mixture composition and method as a component or whole of topical lotions, suntan lotions, creams, shampoos, cleaners, eye drops, hair conditioner, body wash, bath additives and component for internal applications such as drinks, energy drinks, chewing gum, teas, wine-like drink, foodstuffs, herbal supplement pills, spray inhalers and injection.

DESCRIPTION OF THE RELATED ART

Antioxidant and free radical quenching agents have utility in promoting improved cellular functions and maintaining homeostatis. Radical agents are described in the literature as hydroxyl radical (HO.), oxygen (O2), singlet oxygen ($^1O_2$), superoxide anion ($.O_2^-$.) hydroperoxides (HOO.), alkyl peroxides (ROO.), alkyl radical (R.), radical cation (ROH$^+$., R), radical anion (ROH$^-$.). These react in a delirious manner with many types of molecules in the living tissue: proteins, carbohydrates, fats, DNA, RNA etc. There have been implications of high free radical cellular concentrations as a possible indicator or origin of disease. Some conditions believed to be related to high free radical concentration are cancer, heart disease, aging etc.

Many antioxidant compounds used in current topical and internal applications are based on vitamin E and its derivatives (i.e. tocopherol, tocopheryl acetate, tocoretinate and tocotrienol) and similar low water soluble compounds. These compounds are very effective antioxidants and free radical scavengers, but in scavenging free radicals they can form a stable free radical which can increase total free radical concentration in tissue which can result in increased tissue damage. In addition, although many of these compounds have good solubility in cell the fatty, lipophilic portion or cells such as cell membranes, they have poor solubility in the largely aqueous cell interior and intercellular fluid. This poor water solubility inhibits diffusion through multiple layers of cells and into bulk tissue.

Common state of the art techniques used to minimize the antioxidant induced free radical concentration increase are to incorporate additional free radical quenching agents such as vitamin C (ascorbic acid) with the principle radical scavenger. These free radical quenching agents are effective at quenching and reducing the total free radical loading in tissue but have different diffusion rates and different water/oil partition coefficients than the most effective radical scavengers. As in the case of vitamin C they are much more water soluble and not very fat soluble. The differentiation of cellular concentration can result in reduced performance in total free radical reduction in cellular tissue.

A method currently used to increase diffusion into cells is to incorporate "penetration enhances" into products. They molecules contain a hydrophobic portion and a hydrophilic portion. The purpose of these molecules is to diffuse into the fatty acid bilayer cell membrane and disrupt local structure, increase entropy or randomness of the molecules cell wall. Typical molecules are 1-nonyl-1,3-dioxolane, 4-methylcinnaminic acid 2-ethylhexyl ether etc. This allows greater permeation of other components through the membrane and into the cell cytoplasm. This method is advantageous in increase total diffusion rate, but there are disadvantages: molecules of different cellular solubilities will still diffuse at different rates and therefore give significantly different individual component concentrations in different environments in the cell. This may inhibit the total quenching of free radicals by a low water solubility and high water solubility combination pair (i.e. vitamin E and vitamin C).

Another side effect of using "penetration enhancers" is they increase the mobility of toxic or trace carcinogenic materials that may be present in formulations. Many common commercially available goods contain toxic materials from natural and man made sources. Example of moderately toxic materials would be some penetration enhancers. Examples of trace carcinogenic materials would be nitrosamines, 1,4-dioxane, ethylene oxide, polyaromatic hydrocarbons, formaldehyde and acrylamide. Use of penetration enhancing agents increase the cellular concentration of these toxic materials and may therefore make a low toxic material effectively moderately toxic and a low concentration of high toxic material or carcinogens effectively a higher concentration. Concentration enhancement effects may range for a 2 times to 100 times and related delirious symptoms also increased.

Literature indicates that certain plant extracts such as grape seed extracts components of grape seed extract are 50% to 1479% more effective in reducing lipid peroxidation than vitamin C or vitamin E. Increased antioxidant capacity is correlated with increased molecular weight of the antioxidant. Maximum molecular weight of the chemicals tested was 865 grams per mole or three flavonoid trimer. Larson, R. A. (1997) Naturally Occurring Antioxidants. Compounds such as these or of similar nature have been extracted for use by a general extraction method. Nafisi-Movaghar, K et al. U.S. Pat. No. 5,912,363.

It is currently known that cell wall components of microbiological are absorbed and have biological beneficial effect. Glucans have been especially useful in treating skin infection, abrasions, wounds etc. Typical examples would be Kelly, G. E. US Patent 20040082539A1 and the well known use of Aloe Vera mannans. The use of immunomodulating extracts is know in the treatment of cancer and has been found to have immunostimulating properties. Takedo, K. and Okumura, K. (2004) Evidenced-based Complimentary and Alternative Medicine 1(1): 17-27.

The present state of the art does not use a combination of potent antioxidants and immunomodulating substances for treatment of disease or symptoms. Chemical combinations of antioxidants and immunomodulating molecules are not known. Chemical combinations of antioxidants and immunomodulating molecules produced by a simple extraction method are also not known.

In addition, the current state of the art for burn treatment has not progressed significantly in the last 25 years. Mortality has decreased by a factor of roughly two, but this is due to refinement of known techniques and procedures and not principally due to introduction of new and improved techniques.

The current art therefore has a need for improved antioxidant formulations which are nontoxic, do not cause allergic reactions, have high antioxidant activity, have free radical quenching ability, are effective at low concentration and posses moderate to good diffusion through multiple cell layers. There is a need for delivery of antioxidant and/or immunomodulating molecules to the immune system for dispersion throughout the body and concentrating these molecules where they could have the most effect. In particular there is a need for more effective treatment of burns and other topical inflammation.

SUMMARY OF THE INVENTION

The present invention generally relates to mixtures that have free radical quenching ability, diffuse also through the skin or internal tissues readily and are nontoxic. The antioxidants react with energetic radical species and interact with certain protein kinases to improve response to many disease or injury conditions. Optionally the invention discloses the interaction of microbiological and biological extract components that synergistically interact to improve homeostasis in living systems. The microbiological cellular components also diffuse through the skin or tissue and are taken up internally by active pathways. The microbiological components modulate the immune system by interacting with certain cellular receptors designed to bind to these components. Using both types of molecules, free radical quenching and microbiological, or combining both functions into one molecule or combining two molecules by non-bonding interactions produce enhanced effect on disease conditions. The mixtures are made from combination of mostly plant materials that contain flavonoids, proanthrocyanidins, ascorbic acid, tannins, gallates, proteins, fats and plant active materials with the optional related compound or addition compounds of naturally occurring or inoculated microbe such as bacteria, blue-green algae, algae, mycobacteria, spirochete, yeast or fungus to the mixture.

Other aspects, features and advantages of the invention will be more fully apparent from the ensuing disclosure and appended claims.

DETAILED DESCRIPTION OF THE INVENTION, AND PREFERRED EMBODIMENTS THEREOF

The present invention contemplates mixture extracts that are useful for addition to products for internal and external use. In addition the present invention covers use of the extract or concentrated extract as for internal and external application in neat, undiluted form. Further, the present invention contemplates methods of extracting the active ingredients from biological materials.

Compositions of the invention may be embodied in a wide variety of specific formulations, as hereinafter more fully described.

In all such compositions, wherein specific components of the composition are discussed in reference to weight percentage ranges including a zero lower limit, it will be understood that such components may be present or absent in various specific embodiments of the composition, and that in instances where such components are present, they may be present at concentrations as low as 0.001 weight percent, based on the total weight of the composition in which such components are employed.

The present invention has primary active components with contain phenoxy groups. One of the most active compounds is the flavonoid group. Typical extracts of the flavonoid group are somewhat unstable to oxidation and lose their antioxidant ability upon expose to air through standard oxidation mechanisms. The typical method of stabilizing these compounds is by co-pigmentation where flavonoid compound are concentrated and stack with each other and are more stable to oxidation. The aspect that is not covered in the industry is use of other plant extracts to aid in co-pigmentation. Typical compounds used are other largely tannin based compound that are derived from nuts or similar sources. Additionally flavonoids are known to complex with many protein sources. These complexes are bound to the exterior of the co-pigmentation flavonoid stack and render extra stabilization. Flavonoids extracts are known to bind to many proteins to influence cellular activity. The combination of tannin extracts, flavonoid extracts and protein extracts may give additional stability in the active flavonoid extract.

In addition the plant extract in particular the grape seed extract contain naturally occurring yeast and bacteria which promotes redox reactions consume sugar of the plant extract and promote redox reactions to the flavonoid extract and lead to less oxidized stacked flavonoid molecules. The optimum extraction process uses limited oxygen exposure and partial oxidation and cleavage of flavonoid polymer molecules (proanthrocyanidins) with rearrangement to a very active and well absorbed flavonoid species (anthrocyanins) which are assembled into to a stacked co-pigmentation process and additionally stabilized by protein molecules bound on the outside of the co-pigmentation stack.

Agglomeration of flavonoid co-pigments is also assisted by the presence of metal ions. The metal ions form chelation complexes to the flavonoid ring or phenoxy residue. These compounds act as bridging agents that promote higher stability constants. The typical source of could be the extraction fluid, plant, animal or mineral source.

It was found that the use of ascorbic acid improved topical results of the mixture combination. This is likely due to a combination of sacrificial oxidative protection ascorbic acid provides the other antioxidant compounds and ability of ascorbic acid to stimulate tissue collagen regeneration. An effective formulation for solvent extraction has the following components:

| Component | % by weight |
| --- | --- |
| Anthrocyanin/Proanthrocyanidin source(s) | about 1% to about 60.0% |
| Ascorbic acid source(s) | about 1% to about 50.0% |
| Tannin or gallic acid source(s) or polymeric gallic acid sources | about 1% to about 50.0% |
| Immunomodulation molecule source(s) | 0.00% to about 20% |
| Fat(s) source | 0.00% to about 20.0% |
| Protein source(s) | 0.00% to about 50.0% |
| Acidification/buffering agent(s) | 0.00% to about 20.0% |
| Sulfur absorbing compound(s) | 0.00% to about 5.0% |
| Biocide(s) | 0.00% to about 5.0% |
| Fungicide(s) | 0.00% to about 5.0% |

Common anthrocyanin/proanthrocyanidin sources are:

| Common name | Scientific name |
| --- | --- |
| American Elderberry | Sambucus canadensis |
| American Liverwort | Hepatica nubilis |
| Anise | Pimpinella anisum |
| Arnica | Arnica montana |
| Artichoke | Cynara scolymus |
| Ash | Fraxinus species |
| Asiatic Dogwood | Cornus officinalis |
| Barberry | Berberis vulgaris |
| Bilberry | Vaccinium species |
| Birch | Betula species |
| Bittersweet Nightshade | Solanum dulcamara |
| Black Currant | Ribes nigrum |
| Black Locust | Robinia pseudoacacia |
| Black Mulberry | Morus nigra |
| Blackberry | Rubus fruticosus |
| Bog Bilberry | Vaccinium uliginosum |

-continued

| Common name | Scientific name |
| --- | --- |
| Borage | Borago officinalis |
| Buckwheat | Fagopyrum esculentum |
| Burdock | Arctium lappa |
| Butternut | Juglans cinerea |
| Canadian Golden Rod | Solidago canadensis |
| Cat's Claw | Uncaria tomentosa |
| Cat's Foot | Antennaria dioica |
| Catechu | Acacia catechu |
| Chickweed | Stellaria media |
| Cinqefoil | Potentilla erecta |
| Cleavers | Galium aparine |
| Cocoa | Theobroma cacao |
| Cola | Cola acuminata |
| Corn Poppy | Papaver rhoeas |
| Corn Silk | Zea mays |
| Cornflower | Centaurea cyanus |
| Cowslip | Primula veris |
| Date Palm | Phoenix dactylifera |
| Dog Rose | Rosa canina |
| Dragon's Blood | Daemonorops draco |
| Duckweed | Lemna minor |
| English Adder's Tongue | Ophioglossum vulgatum |
| English Hawthorn | Crataegus laevigata |
| English Horsemint | Mentha longifolia |
| English Planatan | Plantago lanceolata |
| Eucalyptus | Eucalyptus globulus |
| European Elder | Sambucus nigra |
| European Golden Rod | Solidago virgaurea |
| European Peony | Paeonia officinalis |
| Eyebright | Euphrasia officinalis |
| Field Scabious | Knautia arvensis |
| Figwort | Scrophularia nodosa |
| Gambir | Uncaria species |
| German Sarsaparilla | Carex arenaria |
| Ginkgo | Ginkgo biloba |
| Goutweed | Aegopodium podagraria |
| Grape | Vitis vinifera |
| Great Burnet | Sanguisorba officinalis |
| Greek Sagg | Salvia triloba |
| Green Tea | Camellia sinensis |
| Heartsease | Viola tricolor |
| Heather | Calluna vulgaris |
| Herb Robert | Geranium robertianum |
| Hibiscus | Hibiscus sabdariffa |
| High Mallow | Malva sylvestris |
| Holly | Ilex aquifolium |
| Hollyhock | Alcea rosea |
| Horse Chestnut | Aesculus hippocastanum |
| Horsetail | Equisetum arvense |
| Houseleek | Sempervivum tectorum |
| Jacob's Ladder | Polemonium caeruleum |
| Jujube | Zyzyphus jujube |
| Knotweed | Polygonum aviculare |
| Lady's Mantle | Alchemilla vulgaris |
| Lemon Balm | Melissa officinalis |
| Lemon Verbenta | Aloysia triphylla |
| Licorice | Glycyrrhiza glabra |
| Lime | Citrus aurantifolia |
| Linden | Tilia species |
| Loosestrife | Lysimachia vugaris |
| Lotus | Nelumbo nucifera |
| Lungwort | Pulmonaria officinalis |
| Lycium Berries | Lycium barbarum |
| Maidenhair | Adiantum capillus-veneris |
| Marigold | Calendula officinalis |
| Marsh Blazing Star | Liatris spicata |
| Meadowsweet | Filipendula ulmaria |
| Milk Thistle | Silybum marianum |
| Moneywort | Lysimachia nummularia |
| Mountain Avens | Dryas octopetala |
| Mouse Ear | Pilosella officinarum |
| Mullein | Verbascum densiflorum |
| Night-Blooming Cereus | Selenicereus grandiflorus |
| Northern Prickly Ash | Zanthoxylum americanum |
| Oak | Quercus robur |
| Oats | Avena sativa |
| Olive Leaves | Olea europaea |

-continued

| Common name | Scientific name |
| --- | --- |
| Onion | Allium cepa |
| Opium Antidote | Combretum micranthum |
| Oregano | Origanum vulgare |
| Oriental Arborvitae | Thuja orientalis |
| Orris | Iris species |
| Osage-orange | Maclura pomifera |
| Oswego Tea | Monarda didyma |
| Ox-Eye Daisy | Chrysanthemum leucathemum |
| Parsley | Petroselium crispum |
| Passion Flower | Passiflora incarnaate |
| Pellitory-of-the-Wall | Parietaria officinalis |
| Peppermint | Mentha piperita |
| Periwinkle | Vinca minor |
| Poley | Teucrium polium |
| Potentilla | Potentilla anserina |
| Premorse | Scabiosa succisa |
| Propolis | NA |
| Purple Loosestrife | Lythrum salicaria |
| Rasberry | Rubus idaeus |
| Red Cabbage | Brassica oleracea |
| Red Currant | Ribes rubrum |
| Red Mulberry | Morus rubra |
| Reed Herb | Phragmites communis |
| Rhatany | Krameria triandra |
| Rose | Rosa gallica |
| Saw Palmetta | Serenoa repens |
| Scotch Thistle | Onopordum acanthium |
| Scullcap | Scutellaria lateriflora |
| Sea Buckthorn | Hippophae rhamnoides |
| Shepherd's Purse | Capsella bursa-pastoris |
| Speedwell | Veronica officinalis |
| St. John's Wort | Hypericum perforatum |
| Stinging Nettle | Urtica dioica |
| Strawberry | Fragaria vesca |
| Tarragon | Artememisia draculnulus |
| Uva-Ursi | Arctostaphylos uva-ursi |
| White Lily | Lilium candidum |
| White Mulberry | Morus alba |
| White Nettle | Lamium album |
| Willow Herb | Epilobium species |
| Witch Hazel | Hamamelis virginiana |
| Woundwort | Stachy palustris |
| Yellow Toadflax | Linaria vulgaris |
| Yerba Santa | Eriodictyon californicum |

Anthrocyanin/proanthrocyanidin can be more broadly defined as condensed tannin sources. Preference on source selection is given to plants with low toxicity.

Common ascorbic acid sources are:

| Common name | Scientific name |
| --- | --- |
| Acerola | Malpighia glabra, M. puniciolia |
| Camu-camu | Myrciaria dubia |
| Kakadu plum | Terminalia ferdinandiana |
| Rose hip | Rosa canina |
| Wolfberry | Lycium barbarum, L. chinense etc. |

Ascorbic acid from manmade sources can also be used.

Common tannin or gallic acid sources or polymeric gallic acid sources are:

| Common name | Scientific name |
| --- | --- |
| Gallnut | Various |
| Nutshells | Various |
| Bark | Various |
| Wood | Various |

-continued

| Common name | Scientific name |
| --- | --- |
| Pine Cones | Various |
| Pine needles | Various |
| Walnut shells | *Juglans* species |
| Walnut | *Juglans* species |
| Oak | *Quercus* species |
| Hickory | *Carya* species |
| Sassafras | *Sassafras albidum* |

Tannin or gallic acid/polymeric gallic acid sources can also be defined as hydrolysable tannins. The overriding selection principle in choosing tannin sources is selecting sources that do not induce inflammation due to trace extractable components or if inflammatory extractable components can be volatilized or degraded by microbial digestion.

Common immunomodulation molecule sources are plant, animal, fungus, mushroom, blue-green algae, algae, mold, microbe, bacteria and yeast materials. These produce or contain immunomodulation molecules such as: glucans, glycans, lipopolysaccharides, lipoteichoic acids, teichoic acid, peptidoglycans, lechtins, lentinans, ornithine-aminolipids, sulfonolipids, mycolic acids, cord factors, gangliosides, acemannan, algin, alginic acid, glucomannan, galactomannan, zymosan and polysaccharides.

The purpose of immunomodulating molecules is to induce cellular response and with possible combination of antioxidant molecules with immunomodulating molecules lead to an extended cellular response. Example would be immune system neutrophils generate free radicals mostly as peroxide and hydroxyl radicals in response to cytokines and other stimulus. These radical oxidizers diffuse to affect healthy and target cells. If the neutrophil had an immunomodulating molecule functionalized with an antioxidant then this might be displayed on the neutrophil's surface and peroxide radicals or hydroxyl radicals would diffuse to and make the bound antioxidant in the free radical form. The neutrophil would have a greater functional oxidation potential on its surface to kill or destroy pathogens when it is physically bound to (the function of the immune system is to seek and destroy invaders) and less free radicals would diffuse out to surrounding areas to harm normal, healthy cells. The general benefits of this are increased concentration of free radicals around the immune cell and therefore increased free radicals presented to the pathogenic organism and increased immunity. Another benefit is decreased inflammation of the whole tissue because of decreased global concentration of free radicals.

Common fat sources are nuts, vegetable oils, fish oils and animal oils.

Common protein sources are:

| Common name | Scientific name |
| --- | --- |
| Amaranth | *Amaranthus* species |
| Buckwheat | *Fagopyrum esculentum* |
| Carob | *Ceratonia siliqua* |
| Flax | *Linum usitatissimum* |
| Millet | Various |
| Quinoa | *Chenopodium quinoa* |
| Sesame | *Sesamum indicum* |
| Sorghum | *Sorghum* species |
| Teff | *Eragrostis tef* |

Protein sources are selected to be non-gluten containing to prevent allergic reaction to susceptible individuals. The Amaranth plant and grain may have additional benefits due to its betalain and betalain derivative content in addition to high quality protein content. Likewise sorghum high lignan content makes it an attractive protein source.

Common sulfur absorbing compounds are colloidal silver and colloidal gold. These substances complex with hydrogen sulfide, thiol compounds and sulfur compounds in the extraction to reduce odor. They also may play a role in the reaction of sulfur compounds with flavonoids and flavonoid cations.

A particularly effective method of extracting beneficial species from the plants is by an acidified aqueous extract at moderate temperatures. This method of extracting produces water soluble compounds in solution such as ascorbic acid, sugars, polysaccharides, water soluble flavonoids (i.e. kaempferol, quercetin, fisetin, myricetin, fustin, catechin, epigallocatechin, epigallocatechin gallate etc), flavonoid monosaccharides, flavonoid disaccharides, flavonoid trisaccharides, flavonoid tetrasaccharides, tannins (i.e. pentagalloylglucose, tirucallin A, oenothein B, glansrin C etc.), tannin saccharides, tannin polysaccharides, gallic acid, ellagic acid, hexahydrodiphenic acid, chebulic acid, caffeic acid, chlorogenic acid, ferulic acid, p-coumaric acid, sinapic acid, water soluble polyphenols (i.e. phloridzin, resveratrol etc.), betalains (i.e. amaranthine, isoamaranthine etc.), pyranoanthrocyanins, and apocyins. Another benefit of acidic water extraction is a reduced level of phenolate anions which are very sensitive to oxidation to semiquinones. The use of acidic medium decreases unwanted oxidation and allows the phenols to be delivered intact to tissue where the pH is slightly alkaline and its antioxidant and radical quenching properties can be useful.

The polymeric proanthrocyanidins of plants are can contain up to 70 repeat flavonoid units. High molecular weight antioxidants such as these are difficult to dissolve in water. The use of moderately acidic water based extraction with extended plant contact time can cleave the oligomeric proanthrocyanidin bonds to form catechin and anthrocyanidins in the presence of a small amount of oxygen. Bruneton, J. (1999) Pharmacognosy 383. All species are in equilibrium but this allows insoluble compounds that may have difficulty diffusing in tissue to be digested to smaller oligomers or monomers which are soluble and readily diffuse through tissue. Another chemical conversion under acidic water extraction is the addition of phenylpropylene groups to flavonoids. The ideal pH for this reaction is slightly acid. There is the formation of an ester linkage and carbon carbon bond by proton abstraction and nucleophilic addition. This coverts caffeic acid and related derivatives to compounds such as cinchonains Ia, Ib, Ic and Id by reaction with flavonoids. These compounds are little studied but have beneficial antioxidant properties.

Compound extracted from plants such as phenols, polyphenols and tannins of this invention interact with many cell types, receptor and disease conditions. The principle methods of interaction are by three pathways: antioxidant or free radicals chain reaction quencher, effect on enzyme systems and modulation of the immune system or cellular signaling systems. Almost every type of cellular system is modulated to a limited or greater extent by these compounds. The flavonoid compounds have been recognized as anti-inflammatory, antioxidant, antiallergic, hepatoprotective, antithrombic, antiviral and anticarcinogenic. Elliot Jr., E., Kandaswami, C. and Theoharides, T. C. (2000) The American Society for Pharmacology and Experimental Therapeutics 52(4): 673-751. They have also been known as general vascular protectors and to simulate hair growth. Both flavonoids and tannins stimulate the enzyme proline hydroxylase which crosslinks collagen fibers and improves collagen strength and growth. Tannins also bind to proteins by covalent and non-covalent bonds and can form protective barrier in a wound or burn. Some flavonoids have analgesic effect in periphery and central nervous system. Lee, B., Jung, S., Lee, J. et al. (2005) Molecules and Cells 20(1): 69-73. The combined ability to promote collagen growth, form a protective layer and reduce pain make plants extracts ideal for treatment of burns and wounds.

Another not so common method of influencing the reaction of disease or trauma is the use of microbiological components to modulate the immune system. The principle components most often used are lipopolysaccharides (LPS) from gram-negative bacteria, lipoteichoic acid (LTA) and peptidoglycan (PG) from gram-positive bacteria and glucans and PG from mold, yeast or fungus. These are components of the cell wall of microbes that the body is sensitive due to the importance of combating bacteria or fungus infection. Use of components of bacteria or fungus/mold that are not virulent or have been chemically, physically or thermally altered to have reduced virulence is an effective method of inducing immuno-modulation. Typical examples of immuno-modulation would be decreasing inflammation response in burns, abrasions, heart disease, lupus or arthritis. Other examples would be to decrease the cell preservation factors in cancer cells leading to cancer cell death.

Microorganisms often use natural binding of their cell wall components to down regulate immune response so as to improve survival rate in the host. Typically this is done by binding to Toll-like receptors (TLR) and inducing specific cytokine production. To date there have been 10 TLR discovered in man which are part of the innate immune system. TLRs are located on lymphocytes, monocytes and epithelial cells depending on the particular receptor TLR receptor. The TLR of greatest interest are: TLR1 and TLR2 act together to bind bacterial lipoproteins (PG). TLR2 and TLR6 act together to bind mycoplasma lipoproteins (PG). TLR4 together with possible cofactors CD14 and/or MD-2 bind LPS, LTA, Heat Shock Protein 60, fibronectin, and virus proteins. TLR binding sets off a cascade in the cell through multiple signaling mechanisms (MyD88, MAL, MKKs, JNK, p38, IKK-α, IKK-β etc.) which eventually induce translocation of nuclear transcription factor-κB (NF-κβ) and AP-1 to the cell nucleus. The nuclear activations bind to certain strands of DNA which lead to protein and glycoprotein transcription of cytokines such as Interlukin-1 (IL-1), Inter-lukin-2 (IL-2) . . . IL-25 and tumor necrosis factor alpha (TNF-α), compliment cascade and coagulation cascade. Janssens, S, and Beyaert, R. (October 2003) Clinical Microbiology Reviews 16(4): 637-646, Henderson, B., Poole, S, and Wilson, M. (June 1996) Microbiology Reviews 60(2): 316-341. Cytokines produced affect cells and can induce chemotaxis, metabolic activation, cell proliferation, inhibit cell proliferation, differentiation and apoptosis. One of the primary cytokine responses is induction of immune response to infectious disease. This is typically induction of monocyte free radical production or phagocytosis, nitric oxide formation etc. For the purposes of this invention the primary interest in is the use of cell wall components to induce anti-inflammatory cytokines and response and as a means of presenting antioxidant molecules to the immune system by cell wall/antioxidant bond formation.

The principle anti-inflammatory cytokines are IL-1ra, IL-4, IL-10, IL-13 and TGF-β. Certain bacteria and fungi components actually stimulate the anti-inflammatory cytokine response and are useful in treating disease. Gram-negative bacteria induce anti-inflammatory interlukin-10 from human monocytes, stimulated B-cell maturation and antibody production and show lower production inflammatory interlukin-12 as compared to gram-positive bacteria. Hessle, C., Andersson, B. and Wold, A. E. (June 2000) Infection and Immunity 68(6): 3581-3586. LTA inhibits Interlukin-2 (an inflammatory cytokine) function by direct binding of IL-2. Plitnick, L. M., Jordan, R. A., Banas, J. A., Jelley-Gibbs, D. M., Walsh, M. C., Preissler, M. T. and Gosselin, E. J. (September 2001) Clinical and Diagnostic Laboratory Immunology 8(5): 972-979.

Most of the body's reactions to bacteria and fungi components are of an inflammatory nature. The body uses these mechanisms to ride itself of virulent pathogens. Pathogens is defined as being able to proliferate in the host despite host defenses such as skin or epithelial cells, antimicrobial secretions, lysozymes in tears, low pH stomach acid, protein in blood and leucocytes in the body. The use of non-virulent or chemically or physically mediated strains of microbes is required so as not to induce infection. Although the use of virulent purified and highly quantified (i.e. reverse osmosis, chromatography, selective antigen binding purification and release, etc.) may be justified in treatment of sever diseases by intravenous injection of other direct entry route into the body it also entail its own risk of infection and disease. A more conservative approach in using active immunogenic compounds is to rely on natural food sources as the microbe source. Many microbes are available from cheese, yoghurt, wine etc. that posses immunological response but are less like to results in infection. Examples from cheese are well noted such as *Geotrichum* and *Arthrobacter*. Tsai, G.-J. and Cousin, M. A. (August 1993) Applied and Environmental Microbiology 59(8): 2563-2571, Martin, N., Berger, C., Le Du, C. and Spinnler, H. E. (2001) Journal of Dairy Science 84(10): 2125-2135. *Geotrichum* mold produced an intermediate positive reaction in manna sensitive antibody testing. Rimek, D., Singh, J. and Kappe, R. (July 2003) Journal of Clinical Microbiology 41(7): 3395-3398. Intermediate reaction allows the body to respond to the compound but not produce as extensive inflammatory immune response.

Another cooperative mechanism by which disease may be prevented is by inhibition of the effects of heat shock proteins. Heat shock proteins are generated by cells in response to stress such as heat, oxidized LDL, free radicals, mechanical stress, infection, oxidants, and cytokine stimulation. The primary benefit of heat shock proteins are they control proper folding of other proteins which is vital for cell repair. The undesired effect of heat shock proteins is they can initiate inflammatory responses of the immune system and have been lined to arteriosclerosis, rheumatoid arthritis, sclerosis and some tumors. Soluble heat shock proteins bind to TLR4/CD14 and induce pro-inflammatory reactions. Xu, Q. (July 2002) Arterioscler. Thromb. Vasc. Biol. 22: 1547-1559. Flavonoids decrease heat shock protein expression and possible related injury or disease. Rusak, G., Gutzeit, H. O. and Ludwig-Müller, J. (2002) Food Technol. Biotechnol. 40(4): 267-273. Competitive blocking of TLR4 by non-virulent glucan, LTA and/or LPS may inhibit binding of heat shock proteins to the immune response pathway. Binding must be competitive but not receptor antagonistic. By combining antioxidants and non-virulent microbes it may be possible to suppress the pathogenesis of heat shock proteins. This may be especially important for burn applications where inhibition of the inflammatory response is beneficial but heat shock proteins within the cell cytoplasm are necessary to control protein folding during rebuilding of damaged tissue. Prevention of heat shock protein in the extra cellular environment from stimulating inflammation response by competitive binding of cell surface Toll-like receptors with a non-inflammatory agent would be of great value.

Antioxidants can limit inflammatory responses by other mechanisms. Antioxidants described in the invention also can reduce NF-κβ production by inhibiting tyrosine phosphorylation, an import step in NF-κβ activation. Tyrosine kinase inhibitors decrease inflammation in mice subjected inflammation inducing drugs or cotton implantation. Fatehi, M., Jafarzadeh, M., Fatehi-Hassanabad, Z. and Gholamnezhad, Z. (2006) DARU 14(1): 6-10. Tyrosine kinase inhibitors and antioxidants reduce nitric oxide synthase II induction in retinal epithelial cells by lipopolysaccharides and interferon-γ. Faure, V., Courtois, Y. and Goureau, O. (1998) American Physiology Society C208-C215. Antioxidants inhibit LPS-Toll 4 activation of IL-8 secretion and NF-κB translocation. Ryan, K. A., Smith Jr., M. F., Sanders, M. K. and Ernst, P. B. (April 2004) Infection and Immunity 72(4): 2123-2130. LTA from gram-positive bacteria interact with Toll-like receptor 2 in human tracheal smooth muscle to stimulate phosphorylation of p42/p44 MARK which induces inflammatory cytokines production. Tyrosine kinase inhibitors can attenuate the vast majority of inflammation response cascade. Lee, C., Chien, C. and Yang, C. (2004) Am. J. Physiol. Lung Cell Mol. Physiol. 286: L921-L930. Another mechanism antioxidants limit inflammation response is by inhibiting the COX-2 enzyme. Flavonoids such as (−)epigallocatechin-3-gallate, apigenin and kamempferol inhibited cyclooxygenase-2 (COX-2) and iNOS activation by LPS. Apigenin, a flavone, also blocked NF-κB formation by possible inhibition of IκB-α degradation. Liang, Y., Huang, Y., Tsai, S., Lin-Shiau, S., Chen, C. and Lin, J. (1999) Carcinogenesis 20(10): 1945-1952.

Flavonoids, polyphenols and tannins have been shown to have positive effects on some cancers. Inhibition of F0F1-ATPase/ATP synthase may be a potent inhibitor of tumor growth and angiogenesis in endothelial cells. Polyphenolic compounds such as resveratol, epigallocatechin gallate, kaempferol and tannic acid showed inhibition at micromolar concentrations. Inhibition was shown to be additive between the compounds. Zheng, J. and Ramirez, V. (2000) British Journal of Pharmacology 130: 1115-1123. Many plant polyphenols potentiate cancer cells to chemotherapeutic agents, radiation, enhance drug availability and protect normal cells from chemo/radiotherapy. Garg, A., Buchholz, T. and Aggarwal, B. (2005) Antioxidants and Redox Signaling 7 (11&12): 1630-1647. COX-2 activation and related cell prostaglandins production from oxidative and proinflammatory stimulation is linked to cancer. Suhr, Y. and Kunda, J. (2005) Archives of Pharmacal Research 28(1): 1-15. Tannic acid compound, pentagalloylglucose, arrests human cancer cell division at low concentrations and induce apoptosis. Chen, W. and Lin, J. (April 2004) The Journal of Biological Chemistry 279(14): 13496-13505. One of limiting factors for use of these compounds to treat cancer is limited body uptake and often less than therapeutic concentration is present. Sufficient antioxidant concentration can be delivered to the skin by topical application and to the GI tract by oral ingestion. Combining antioxidants with immunomodulating components may increase adsorption and delivery to target areas to bring concentrations closer to therapeutic levels in more parts of the body.

Endocytosis by specialized antigen presenting M cells is a process where almost any particle with some antigenic property is presented to the immune system. Small microbes and samples of foreign material are delivered by a special series of epithelial M cells that line respiratory and digestive track mucus membranes for presentation of ingested antigens in the intestine. Peyer's patches are organized lymphoid tissue covered in an epithelial layer and follicle-associated envelope (FAE) composed of follicles with B cells and interfollicular area filled with antigen-presenting and T cells. Plant lectins, such as *Sambucus nigra* and *Maackia amurensis* II, can aid the transition of antigens through the M cell. Giannasca, P. J., Boden, J. A. and Monath, T. P. (October 1997) Infection and Immunity 65(10): 4288-4298. Oral administration of antigens generates dendritic cells which are better able to induce T cells to produce anti-inflammatory cytokines IL-4 and IL-10. This effect generates cell-mediated oral tolerance. Iwasaki, A. and Kelsall, B. (July 1999) The Journal of Experimental Medicine 190(2):229-239. The overall general effect of Peyer's patch adsorption is a moderation of inflammatory immune responses. Antigen presenting cells are also located in the skin so topically applied antigens may be transported to the immune system for presentation.

LPS, LTA and fungal incorporation of antioxidants in antigen presenting cells may transfer to blood HDL and LDL reducing atherosclerosis. Another possible delivery path mechanism associated with endocytosis is cross talk to other lymphatic and circulatory system. The material presented to the T and B cells may be presented to other cells in the lymphatic system. Compounds such as LPS and LTA may incorporate antioxidants in their structure if the microbes were grown in a rich, antioxidant environment. Incorporation of antioxidants is known in association with plant cell wall polysaccharides. The plant source flavonoids, polyphenols or phenols functionalized with glucosides, arabosides or polysaccharides may be incorporated into the glycolic portion of the bacterial PG, LPS or LTA or fungal glucan cell walls. A proposed mechanism of this incorporation is as follows: During acid based cleavage of proanthrocyanidins a carbocation is formed. The carbocation will react with any nucleophile to generate an addition product by covalent bond formation and proton loss. Typical nucleophiles are alcohols, amines or thiols. The flavonoid carbocation could react with an amine group of amino acid in LTA or PG to form an amine adduct, an alcohol group of the saccharides in LPS, LTA, PG or glycan to form an ether or a thiol group bound to a microbe or bound to a sulfur adsorbing particle such as colloidal silver or gold to form a thiol derivative. This allows for the covalent functionalization of microbe components by antioxidants. A method of antioxidant functionalization of immunomodulating by hydrogen bond formation would be the reaction of tannins or condensed tannins with microbial proteins. The importance of this as far as M cell incorporations is based on the ability of M cells to incorporate these antigens and the ability of the immune system to shuffle LPS, LTA and PG related compounds to VLDL, LDL and HDL particles in the blood. Lipoteichoic acid (LTA) an immunostimulant glycolipid of gram-positive bacteria is bound in >95% efficiency in plasma lipoproteins. Distribution for LTA is HDL 68%±10%, LDL 28%±8% and VLDL 4%±5%. Levels, J. H. M., Abraham, P. R., van Barreveld, E. P., Meijers, J. C. M. and van Deventer, S. J. H. (June 2003) Infection and Immunity 71(6): 3280-3284. Soluble serum protein CD14 and lipopolysaccharide binding protein (LBP) synergistically interact to break lipopolysaccharides (LPS) into smaller units and transfer them into high density lipoproteins (HDLs). Wurfel, M. M., Hailman, E. and Wright, S. D. (May 1995) The Journal of Experimental Medicine 181: 1743-1754. VLDL, LDL and HDL lipids can be reservoirs for functionalized LTA, LPS or GP.

Heart disease is associated with inflammatory response of the immune system and related to the initial build-up and oxidation of LDL inside the artery wall (intima). The oxidized LDL stimulates monocyte adhesions and secretion of inflammatory cytokines. The monocytes mature into macrophages and engulf the oxidized LDL particles. The macrophages become frothy-like because of the fatty LDL ingested. A plaque cap develops over the intima in the inflammation process. The plaque fills part of the artery, reducing blood flow. The inflammatory molecules may break the cap and secret clotting factor. This process may make a thrombus which can clog the artery or the thrombus may flow to other areas and clot there causing a stroke. Libby, P. (May 2002) Scientific American 286(5): 47-55. The incorporation of antioxidants in LDL molecules by use of M cell adsorption of phenoxy functionalized microbes makes the initial inflammatory reaction less likely and could possibly reduce total cardiovascular disease. The ability of phenoxy compounds to inhibit lipid oxidation is well documented. Schewe, T., Kühn, H., and Sies, H. (2002) Journal of Nutrition 132: 1825-1829. The possibility of using the M cell transport mechanism to deliver functionalized antioxidants, anti-inflammatories and/or immunomodulants has not been documented before. It possibility is implied because of the ability to incorporate antioxidants in microbe cell walls. Vasserot, Y., Caillet, S, and Maujean, A. (1997) Am. J. Enol. Vitic. 48: 433-437.

Another possible use of a functionalized microbe particle as described above is for the delivery of bioactive ingredients to known specific sites to treat disease. Such particles would have to be free of non-desirable antigens, have reasonable half life in the body and deliver drug molecules at a controlled rate and site and be biodegradable. General requirements of a "biologically active polymer-polymer therapeutic system" were published by Moghimi, S. M., Hunter, A. C. and Murry, J. C. (2001) Pharmacological Reviews 53(2): 283-318. The present invention contemplates such molecules/particles using a flavonoid/tannin/plant compound functionalized microbe(s) or portion of a microbe(s). Other functional groups could be used in place of the above mentioned and synthetic methods can be used to assure high degree of functionalization.

Another important function of bacteria and fungi is the simple degradation of flavonoid, polyphenol of phenol saccharides and polysaccharides to the free flavonoid and lower molecular weight phenols and polyphenols. The free compounds are usually adsorbed through the small intestine to a much higher extent than high molecular weight polyphenol derivatives. Déprez, S., Brezillon, C., Rabot, S., Phillippe, C. Mila, I., Lapierre, C. and Scalbert, A. (2000) Journal of Nutrition 130: 2733-2738. After ingestion high molecular weight polyphenols are usually degraded in the large intestine by microflora and then absorbed. Degradation of high molecular weight compounds prior to digestion would allow adsorption though the entire digestive system and increase total adsorption efficiency. Overall the ideal goal would be to have a mixture of relatively low molecular weight antioxidants for non-specific/specific adsorption and high molecular weight glycans, PG, LPS and/or LTA molecules functional with antioxidants for M cell active adsorption or other type of active adsorption.

The features and advantages of the invention are more fully illustrated by the following non-limiting examples, wherein all parts and percentages are by weight, unless otherwise expressly stated.

EXAMPLES

Typical extraction is outlined. Two 99.9% silver wire electrodes were place in 17,700 g well water. A DC current of 12.5 mA was run through the electrodes for one hour to give approximately 2.8 ppm colloidal silver. The colloidal silver solution was transferred to a 304 stainless steel container and 300 g of lemon juice, Citrus x limon juice was added. A nylon sock was loaded with the following well mixed plants:

TABLE 1

| Component | Weight | Weight % |
| --- | --- | --- |
| Red grape seed, dried, *Vitis vinifera* seed | 276 g | 29.8% |
| Amaranth plant, dried, *Amaranthus gangeticus* | 44 g | 4.75% |
| Amaranth flour, *Amaranthus* genus species unknown | 44 g | 4.75% |
| Rose hips, dried, *Rosa canina* fruit | 195 g | 21.1% |
| Elder berry, dried, *Sambucus canadensis* fruit | 171 g | 18.5% |
| Walnuts, whole crushed, *Juglans regia* whole nut | 196 g | 21.1% |

The sock was tied closed and placed in the water/colloidal silver/lemon juice solution. The stainless steel vessel was covered and heated and maintained at 50 C. At least once a day the nylon sock was mechanically kneaded to improve extraction. After the 4th day the nylon sock was removed and the extract filtered through a 1 micron polypropylene depth filter (Pentek BP-420-1) into a polyethylene container with minimal head space. The extraction of the same plant materials with colloidal silver/lemon juice/water was done twice more as described above. All the extracts were combined after filtration. pH was 4.1 and total solids were 0.22%. Total yield with some water evaporation was 41,000 g. The solution was allowed to sit for 5 days and the following naturally occurring microbes developed in the solution:

TABLE 2

| Bacteria | Fungus/Mold |
| --- | --- |
| *Chryseobacterium indologenes* | *Geotrichum* sp. |
| *Bacillus* sp. | |
| *Acetobacterium* sp. | |

The extract was mixed in the following volume percentages to make test products:

TABLE 3

| Component | Lotion A | Lotion B | Foamer | Shampoo | Neat |
| --- | --- | --- | --- | --- | --- |
| Extract example 1 | 20% | 20% | 33% | 20% | 100% |
| Cocoa Butter Hand and Body Lotion, PARA Laboratories, Hempstead, NY | 80% | — | — | — | — |
| Vaseline Intensive Care Advanced Healing Skin Protectant Lotion, Unilever, Trumbull, CT | — | 80% | — | — | — |
| Well Water | — | — | 34% | — | — |
| Antibacterial Liquid Hand Soap, Western Family Foods Inc, Portland, OR | — | — | 33% | — | — |
| Suave Natural Shampoo, Unilever, Trumbull, CT | — | — | — | 80% | — |

It should be noted that the extract can be used in neat form, mixed into or mixed in at time of manufacturing of commercial consumer formulations.

Foamer solution was dispensed using an F-2 pump foamer supplied by McKermam Packaging Clearing House.

Lotion testing on sunburns. 4 individuals were tested. Individual 1 was a fair skinned Caucasian female who burns easily, 30 yrs old. She had a red face from sunburn. Lotion A was applied topically 5 times in the course of several hours. No sunburn was detected the next day. No pealing of skin was detected. Individual 2 was a Caucasian male, 40 yrs old who been skiing at 7,000 foot elevation for 7 hours during a cloudless day with no sunscreen or face or head protection. After skiing the initial signs of sunburn and windburn were noted. Lotion B was applied topically 5 times to the affected areas of the skin over a 2 hour period. Redness and irritation subsided within an hour. A slight amount (<5%) of facial skin pealed in 5 days. Individual 3 was a Caucasian male, 37 years old, with the initial signs of sunburn; reddening of skin, skin inflammation and slight pain. Lotion B was applied topically twice and sunburn, inflammation and pain subsided with minutes. Individual 4 was a fair skinned Caucasian female, 38 years old with the initial signs of sunburn; reddening of skin, skin inflammation and slight pain. Lotion B was applied topically twice and sunburn, inflammation and pain subsided with minutes.

Testing on burns. 2 individuals were tested. Individual 1 was a 52 year old male with a second degree heat burn on thumb and index finger from the same event. Initially the index finger was purposefully not treated to show difference in foamer effectiveness in burn treatment. Foam from Foamer was applied topically every 15 minutes immediately after thumb burn for 1 hour, then every half hour for 2 hours, then every 1-2 hours for 4 hours. The next day the foamer was applied every 3-4 hours. No burn, scar or blister were noted on the thumb during any time of the Foamer application or thereafter. Pain relief from the burn occurred within several minutes of the initial application. The index finger had formed a blister during this time and was treated on the third day with Foamer applied topically every 4 hours for 1 day. Index finger blister went away in one day, although there was a slight scar remaining. Second individual was a 59 year old diabetic male with sever frostbite on his feet. After cold exposure his feet were 3-4 times normal size. Clinical diagnosis characterized the injury as a third degree burn of approximate area of 15-20% of one foot. Neat extract was sprayed on the injury every half hour during the day for the first week with addition topical application of Lotion A several times a day. The injury was approximately 50% resolved in 7 days. The individual sprayed neat extract every 2 hours during the day on the injury for the next 2 weeks. Daily topical application on Lotion A was also used. At day 21 the injury was healed with no scar but a slight discoloration of the skin where the third degree burn had been.

Treatment of Prurigo Nodularis. A female 45 years of age had been diagnosed with Prurigo Nodularis and had the condition for 12 years. The condition was severe and covered 30-50% of her body. After spraying neat extract and using Lotion A twice a day the condition significantly improved in 6 weeks.

Treatment of psoriasis. A male 60 years of age had been diagnosed with psoriasis on arms, back and legs. He applied Lotion A and Foamer four times a day for 2 weeks. After two weeks the psoriasis was gone. Occasional use of Lotion A was required to prevent return of symptoms.

Although the invention has been variously disclosed herein with reference to illustrative embodiments and features, it will be appreciated that the embodiments and features described hereinabove are not intended to limit the invention, and that other variations, modifications and other embodiments will suggest themselves to those of ordinary skill in the art, based on the disclosure herein. The invention therefore is to be broadly construed, as encompassing all such variations, modifications and alternative embodiments within the spirit and scope of the claims hereafter set forth.

What is claimed is:

1. An anthrocyanin(s)/proanthrocyanidin(s) mixture useful in wound healing comprising a solvent extraction of the following components:

about 1.0% wt.-about 60% wt. anthocyanin/proanthocyanidin sources wherein the anthrocyanin/proanthrocyanidin sources are red wine grape seeds (*Vitis vinifera* seeds) and American elderberry fruit (*Sambucus Canadensis* fruit);

about 1.0% wt.-about 50% wt. ascorbic acid source wherein the ascorbic acid source is rose hips (*Rosa canina* fruit);

about 1.0% wt.-about 50% wt. tannin or gallic acid source or polymeric gallic acid source wherein the tannin or gallic acid source or polymeric gallic acid source is English walnut shells (*Juglans regia* shells);

about 1.0% wt.-about 50% wt. protein source wherein the protein source is Amaranth plant, of any or all of the following species: *Amaranthus gangeticus, Amaranthus hypochondriacus L., Amaranthus hybridus, Amaranthus powellii* and *Amaranthus retroflexus;* about trace amount-about 20% *Geotrichum candidum;* about 1.0% wt.-about 20% wt. fat source wherein the fat source is English walnut nut (*Juglans regia* nut);

about 1.0% wt.-about 20% wt. acidification or buffering agent wherein the acidification or buffering agent is lemon juice (Citrus x limon juice) and about trace amount-about 5% wt. sulfur absorbing compound wherein the sulfur absorbing compound is colloidal silver, wherein the total of the weight percentages of the components of the composition does not exceed 100% by weight.

* * * * *